Figure 3:
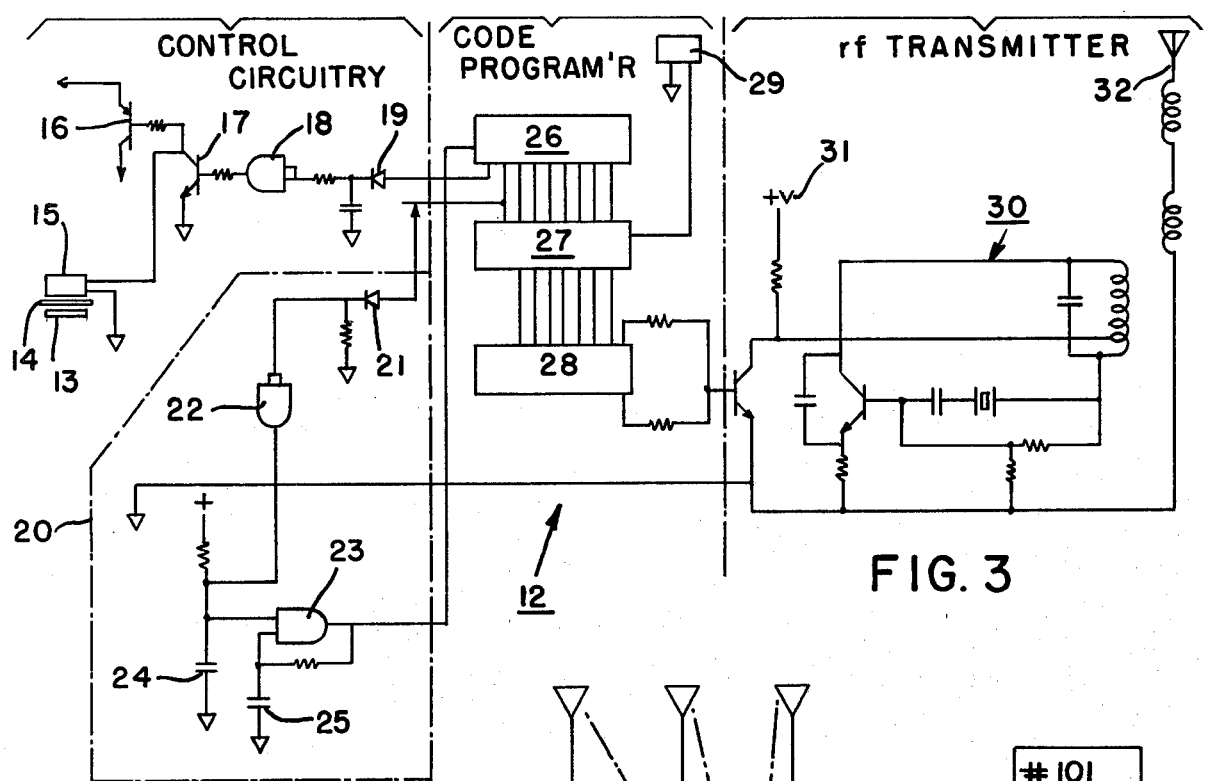

United States Patent [19]

Wright

[11] 4,411,274
[45] Oct. 25, 1983

[54] APPARATUS AND METHOD FOR MONITORING THE OESTRUS CYCLE IN FEMALE ANIMALS

[75] Inventor: Thad F. Wright, Yadkinville, N.C.

[73] Assignee: Agricultural Computer Systems, Inc., Yadkinville, N.C.

[21] Appl. No.: 265,551

[22] Filed: May 20, 1981

[51] Int. Cl.$^3$ ............................................. G07C 11/00
[52] U.S. Cl. ................................. 128/738; 128/775; 128/903
[58] Field of Search .............. 128/340, 419 D, 419 G, 128/419 PT, 738, 748, 775, 903

[56] References Cited

U.S. PATENT DOCUMENTS

| | | | |
|---|---|---|---|
| 3,076,431 | 2/1963 | Rule et al. | 119/1 |
| 3,158,133 | 11/1964 | Larson | 119/1 |
| 3,205,857 | 9/1965 | Larson | 119/1 |
| 3,516,575 | 6/1970 | Moffitt | 222/52 |
| 3,842,802 | 10/1974 | Lang et al. | 119/1 |
| 3,844,273 | 10/1974 | Polson | 128/2 |
| 3,948,249 | 4/1976 | Ambrosini | 128/2 H |
| 4,055,839 | 10/1977 | Skeggs | 340/279 |
| 4,206,766 | 6/1980 | Bielka | 128/738 |
| 4,247,758 | 1/1981 | Rodrian | 128/738 |

OTHER PUBLICATIONS

Buckley et al., "A Telemetry System for Automatically Recording Copulation in Sheep", Medical and Biological Engineering, Nov. 1974, pp. 837–842.

Primary Examiner—Richard J. Apley
Assistant Examiner—George Yanulis

[57] ABSTRACT

The invention herein consists of apparatus and a method of monitoring livestock for artificial insemination purposes. A transmitter is fastened to the female animal to generate a signal which is received at a distant point and recorded for interpretation of the phase of the animal's fertility cycle. The transmitter includes time delay circuitry which causes the transmitter to pause for a predetermined time before signal generation. Switch means when closed activates the transmitting means and cut-off means within the transmitter terminates its activities after signal generation to conserve energy.

In the preferred embodiment of the invention a magnetic switch is employed and a time delay circuit in the transmitter allows approximately 15 seconds to elapse before signal generation. The receiving unit of the preferred embodiment includes a standard receiver and a microprocessor. Signals from the microprocessor are received by an output expander which directs the signals to the appropriate analog switch for reception by a printer.

12 Claims, 4 Drawing Figures

APPARATUS AND METHOD FOR MONITORING THE OESTRUS CYCLE IN FEMALE ANIMALS

BACKGROUND AND OBJECTIVES OF THE INVENTION

Various chemical and electronic devices have been used in the past to aid cattle breeders in determining the start of the standing heat or oestrus cycles of various animals including livestock. Due to the expense involved and the random success obtained many prior art devices have met with only modest acceptance on a commercial scale. The present invention overcomes many of the known problems and provides highly accurate data for a livestock owner so he can utilize with a great degree of success artificial insemination which must be carried out within relatively short time limits.

With the shortcomings of the prior art devices and methods in mind one of the objectives of the present invention is to allow the cattle breeder to pinpoint with a high degree of accuracy the first six hours after the period of standing heat in a female cow terminates.

It is another objective of the present invention to provide a monitoring device which is relatively inexpensive to own and maintain and which can be used with large herds.

It is still another objective of the present invention to provide a standing heat monitoring device which records critical data and includes a printing means whereby the data recorded can be used for future reference.

Another objective of the present invention is to provide data regarding the last simulated mounting during the standing heat cycle so termination of the cycle can be closely approximated.

Yet another objective of the present invention is to provide a transmitter which will conserve energy by transmitting only a series of short bursts after simulated mounting has terminated.

Still another objective of the present invention is to provide a standing heat cycle monitoring device which is useful for large cattle herds, and which allows monitoring the herd from a distant point.

Also a further objective of the present invention is to provide a receiver which operates on standard household current and which is also equipped with an emergency battery backup supply system.

SUMMARY OF THE PREFERRED EMBODIMENT AND DESCRIPTIONS OF THE DRAWINGS

In the preferred embodiment of the present invention an rf transmitting means is mounted on a resilient pad at the rear back portion of the cow to be bred. Underneath the resilient pad is positioned a permanent magnet of suitable strength. When a second cow simulates mounting the first, the second cow's breast bone will apply pressure to the transmitting means thus causing a magnetic switch of the transmitting means to be activated by the flux field of the magnet as the distance is shortened between the switch and the magnet. A time delay circuit in the transmitting means prevents an immediate signal transmission and approximately fifteen seconds will elapse between switch activation and signal transmission. The transmission consists of a burst of three consecutive signals within a few seconds before the transmitting means is then automatically shut-off to conserve energy from its battery supply. Multiple transmitting means can be employed with a single receiving unit and each transmitting means includes a counter and decoder, a coding matrix and a tone generator as part of a code programmer. The code programmer is innerfaced to an rf transmitter of conventional design which relays a particular coded signal to the distant receiving unit. A broadcast frequency of 49.82 megacycles has been found to be adequate and depending upon the terrain and atmospheric conditions the signal can be received without difficulty for up to one-half mile.

The receiving unit for the preferred embodiment includes a standard AM receiver which provides a tone to a tone decoder for relay to a microprocessor. The microprocessor includes a data memory (RAM) which stores data received until requested and a time routine. Communicating with the microprocessor is an address storage for the programmed memory and a programmable memory (ROM). Signals from the microprocessor are received by an output expander which directs the signals to appropriate analog switches for reception by a printing means. By manual activating the printing means the particular transmitting means is identified by a number on a print-out which also shows the time of the burst transmission. Once the printing means has been activated it will continue to demonstrate all the transmitting means which have submitted signals and the times of reception of their transmission burst. In the preferred process of the invention three signals per burst are transmitted and received by the receiving unit having a printing means, and the printing means upon manual activation forms a readable record of the data received after which artificial insemination can be performed at a time selected by the cattle owner.

Figures 1, 2:
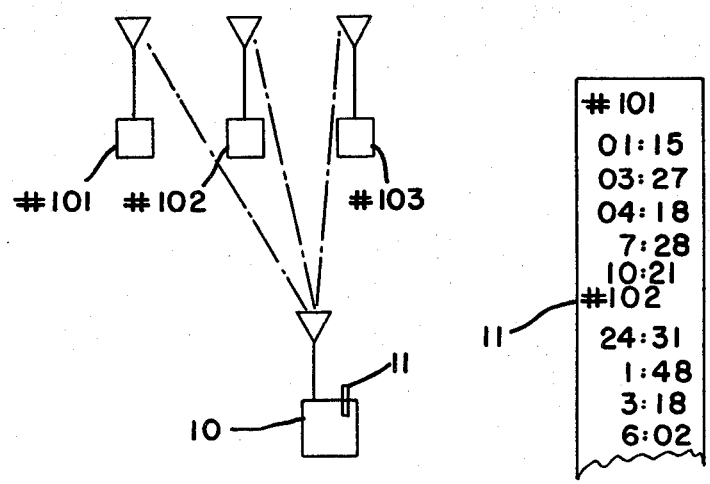
Figure 4:
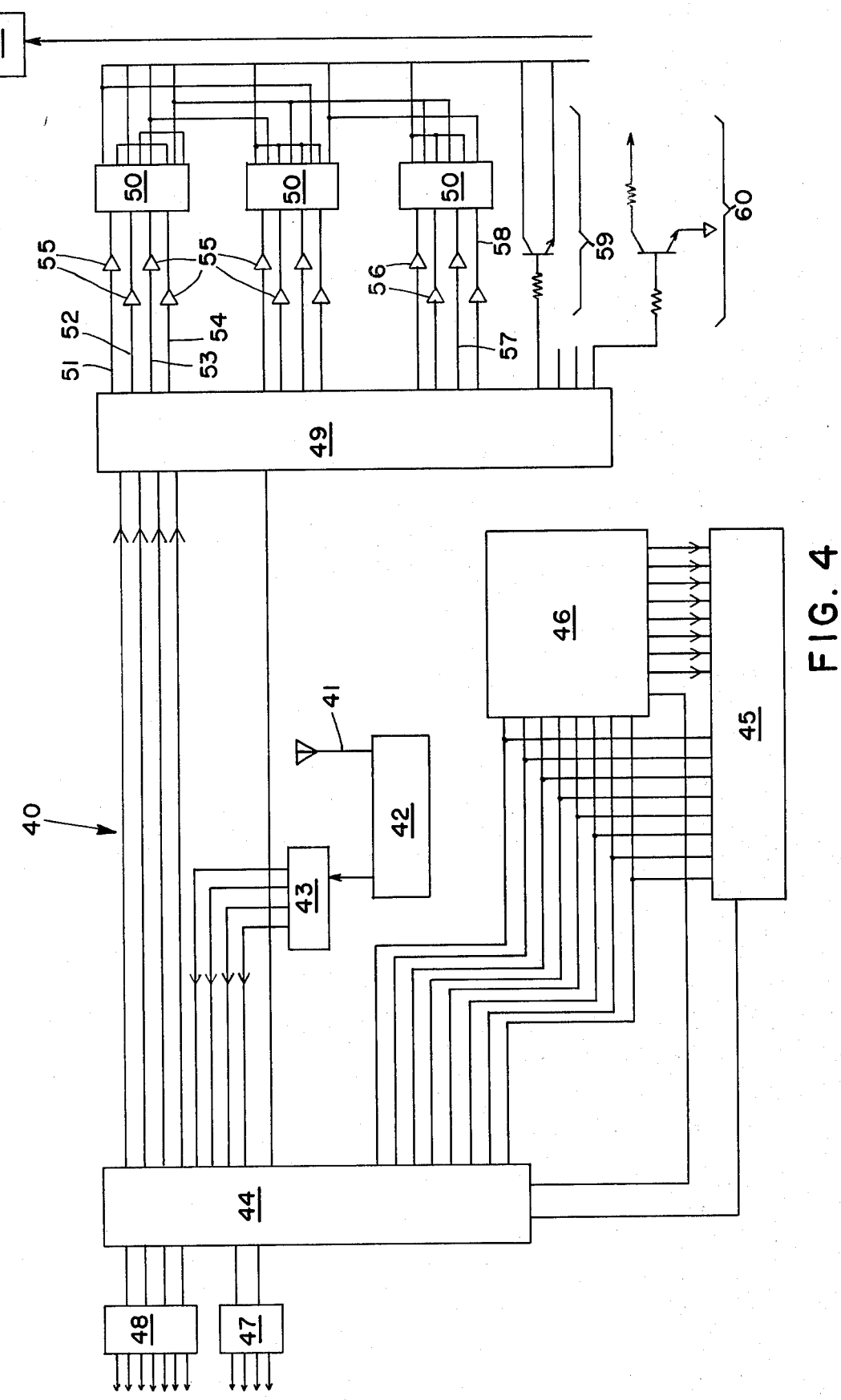

Turning now to the drawings,

FIG. 1 demonstrates a diagrammatic view of the invention;

FIG. 2 represents a portion of a print-out;

FIG. 3 demonstrates a transmitting means as used with the present invention; and FIG. 4 demonstrates a signal receiving unit.

For a more detailed description of the drawings and operation of the invention, in FIG. 1 three transmitting means #101, #102, and #103 are shown transmitting rf signals to receiving unit 10. Print-out 11 is shown in typical fashion in FIG. 2 as would be recorded with a designation of the particular transmitting means and times of burst transmission. A thermal or other printing means may be utilized and along with the time, a date may also be included in the print-out information. As shown in the print-out of FIG. 2 the cow having transmitting means #101 was mounted at 1:15 A.M., 3:27 A.M., 4:11 A.M., 7:28 A.M., and 10:21 A.M. (Mounting herein refers to mounting by a cow usually referred to as simulated mounting.) It has been found by some researchers that artificial insemination is most successfully performed within approximately six hours after the standing heat cycle ends. As generally occurs the standing heat cycle last eight to eighteen hours during which time frequent simulated mountings occur (approximately every 20 minutes) by other cows. Thus, by recording the first and last simulated mountings it is possible to artificially inseminate cows with a high degree of success by doing so within approximately 6 hours of the last recorded simulated mounting or at other time intervals as determined the most effective by the breeder.

As shown in FIG. 2 the cow bearing transmitting means #101 was first mounted at 1:15 A.M., and was last mounted at 10:21 A.M. If at the time of reading the print-out it was fourteen hundred hours (2:00 P.M.) it could be assumed that since no mounting had occurred between 10:21 A.M. and 2:00 P.M., some three and one-half hours, that the standing heat cycle had terminated at approximately 10:21 A.M. Therefore, if one used the six hour time frame, artifical insemination should take place between 10:21 A.M. and 4:21 P.M. for the greatest degree of success of conception.

FIG. 3 demonstrates a transmitting means 12 having magnetic means 13 which may be a permanent magnet contiguous with resilient member 14 which may be sponge rubber or other media. Hall-effect magnetic switch means 15 activates transmitting means 12 when pressure is applied to switch means 15 by the breast bone of the cow performing simulated mounting. Transistor 16 is a PNP transistor which cuts power on and off to transmitting means 12 whereas transistor 17 is an NPN transistor which holds power on transistor 16 until such time as the transmitter has completed three signal bursts. (Three signals of 3 to 8 seconds per signal per burst have been found to be satisfactory although more or less numbers of burst may be utilized if desired). After that, further activation of switch means 15 (another simulated mounting) is required, since switch means 15 is then open, for additional signals to be transmitted. Also shown in the control circuitry is signal switch 18 along with diode 19. Another part of the control circuitry of transmitting means 12 is time delay circuitry 20 which includes diode 21, signal switches 22 and 23 and capacitors 24 and 25. Time delay circuit 20 provides for a time delay between the time switch means 15 is activated and signals are sent to the receiving unit. Fifteen seconds has been found to be a preferrable time delay as by this time the simulated mounting has usually terminated.

Also included in transmitting means 12 is a code programmer section including signal counter and encoder 26, coding matrix 27, and tone generator 28. Safety switch 29 is illustrated which could activate circuitry (not shown) in transmitting means 12 causing it to give, for example, an audio sound if desired in the event the transmitter becomes dislodged and falls from the cow. The safety switch 29 might also produce a distinct rf signal which could be received by a second receiving unit (not shown) which would assist in locating a lost transmitting means.

Transmitting means 12 also includes conventional rf transmitter circuitry 30 including power supply 31 which may be for example a fifteen volt battery pack. A solar cell (not shown) may be attached for charging the battery pack. Transmitting means 30 also includes antenna 32 for transmitting the signal to the receiving unit. The transmitting means 12 may be glued, strapped, or attached by Velcro or by any other method which will provide a secure means of holding the transmitting means 12 to the cow under the adverse conditions of simulated mounting, poor weather or the cow's own muscle movements and behavior.

Signal burst transmitted are received by receiving unit 40 through antenna means 41 as shown in FIG. 4. The signals transmitted have been effective at 49.82 megacycles although other frequencies may be used. The burst received by antenna 41 is directed to the standard AM heterodyne receiver 42 which in turn directs a signal to tone decoder 43. Tone decoder 43 directs a decoded signal to microprocessor 44 such as an Intel 8035 which includes a random access memory (RAM) and a time routine program. Microprocessor 44 has a programmable memory 45 of the "Read Only Type" (ROM) and memory 45 is joined with address storage memory unit 46. Also joined to microprocessor 44 are interface chips 47 and 48 which can be used for a time display module (not shown). Receiving unit 40 is powered by conventional a/c voltage (not shown) and additionally includes a battery pack with self charger (not shown) in case of a power failure.

Burst may be received from one or more of the many transmitting means which may be employed depending on the size of the herd and each particular transmitting means has its own identification number such as #101, #102, or #103 as shown in FIG. 1. Receiving unit 40 could accommodate 40 to 50 transmitters if required. Each transmitting means burst is identified by the microprocessor 44 and is relayed to output expander 49 which then modifies the signal and directs it through appropriate channels and to one or more analog switches 50. For example, channel 51 may provide a signal for printing a "0" whereas 52 may provide the printing of a "1"; 53 a "2"; 54 a "3" and so forth. Signals passing along channels 51 through 54 are increased by amplifiers or buffers 55. Channel 57 may be responsible for the "#" and channel 58 the paper advance ( ↑ ) symbol.

Circuitry 59 prevents the "#" symbol from being printed when not required and circuitry 60 provides power to an indicator light (not shown) on the front of the receiving unit 40 telling the operator that a signal burst has been received and is available for printing. When the indicator light is on, a convenient print-out button (not shown) on the receiver cabinet is pressed which activates printing unit 61. Upon activation of printing unit 61 all signals received and stored are then printed as shown on print-out tape 11 in FIG. 2.

With the activation of the printing means 61 each transmitting means is indicated on the print-out tape along with the time each signal burst was received. After the print-out has been completed the data memory (RAM) of the microprocessor is erased and any new incoming information is stored therein.

A farmer or herdsman can review the tape print-out 11 and determine which cows are ready for artificial insemination as earlier explained. Printing unit 61 may be, for example, a thermal printer as is conventionally employed in calculators and other similar devices.

The examples shown herein are to illustrate the invention and are not intended to limit its scope.

I claim:

1. Apparatus for monitoring the oestrus cycle in female animals comprising: a switch means positioned on the female signal, a transmitting means for attachment to the female animal communicating with said switch means, said transmitting means for generating a long range signal burst, said transmitting means including time delay circuitry, said time delay circuitry preventing signal transmission until a predetermined time lapse occurs from the time said switch means is initially activated independent of the length of switch activation, a receiving unit for receiving signals generated by said transmitting means, said receiving unit including a printing means for recording data from said transmitting means.

2. Apparatus for monitoring the oestrus cycle in animals as claimed in claim 1, wherein said transmitting means includes cut-off means, said cut-off means connected to said switch means whereby power is terminated to said transmitting means after said transmitting means has completed a series of signal bursts.

3. Apparatus for monitoring the oestrus cycle in female animals as claimed in claim 1 wherein said printing means includes control means for directing said printing means to form a print-out demonstrating data from signals received from said transmitting means.

4. Apparatus for monitoring the oestrus cycle in female animals as claimed in claim 1, wherein said transmitting means includes decoding means.

5. Apparatus for monitoring the oestrus cycle in female animals as claimed in claim 1, wherein said receiver unit includes heterodyne receiver, a decoder circuit, in communication with said heterodyne receiver, a microprocessor, said microprocessor communicating with said decoder circuit and said microprocessor communicating with a printing means.

6. A method for monitoring the oestrus cycle in female animals comprising: activating a switch means worn by the female animal, communicating a signal from the switch means to a transmitting means also worn by the female animal controllably delaying the transmission of a signal burst by the transmitting means from the time the switch means was initially activated independent of the length of the switch activation, generating a coded signal burst by the transmitting means for reception, receiving said generated signal at a remote location, deactivating said transmitting means, decoding said signal and forming a print-out from said decoded signal.

7. A method for monitoring the oestrus cycle in female animals as claimed in claim 6, wherein activating switch means comprises applying sufficient pressure to the switch means.

8. A method for monitoring the oestrus cycle in female animals as claimed in claim 7, wherein generating a coded signal burst comprises generating a series of short signals.

9. A method of monitoring the oestrus cycle in female animals as claimed in claim 8, wherein generating a coded signal burst comprises generating three signals having short duration intervals.

10. A method of monitoring the oestrus cycle in female animals as claimed in claim 6, wherein receiving said signal at a remote location comprises: receiving said signal with a heterodyne receiver and subsequently decoding said signal.

11. A method for monitoring the oestrus cycle in female animals as claimed in claim 10 and in including the step of storing the decoded signal in a memory bank for later recall.

12. A method of monitoring the oestrus cycle in female animals as claimed in claim 6, wherein forming said print-out comprises: printing the time and transmitting means identification signal burst received for determining the end of the animal's standing heat cycle.

* * * * *

UNITED STATES PATENT AND TRADEMARK OFFICE
CERTIFICATE OF CORRECTION

PATENT NO. : 4,411,274

DATED : October 25, 1983

INVENTOR(S) : Thad F. Wright

It is certified that error appears in the above-identified patent and that said Letters Patent is hereby corrected as shown below:

Column 4, line 55, "signal" should read -- animal --.

Signed and Sealed this

Third Day of April 1984

[SEAL]

Attest:

GERALD J. MOSSINGHOFF

Attesting Officer

Commissioner of Patents and Trademarks